(12) United States Patent
Kraemer et al.

(10) Patent No.: US 7,838,500 B2
(45) Date of Patent: *Nov. 23, 2010

(54) CRYSTALLINE FORM OF 1'-(1-METHYLETHYL)-4'-[(2-FLUORO-4-METHOXYPHENYL)METHYL]-5'-METHYL-1H-PYRAZOL-3'-O-β-D-GLUCOPYRANO-SIDE, A METHOD FOR ITS PREPARATION AND THE USE THEREOF FOR PREPARING MEDICAMENTS

(75) Inventors: Gerd Kraemer, Eberhardzell (DE); Hans-Juergen Martin, Biberach (DE); Gebhard Adelgoss, Biberach (DE); Klaus Dugi, Dresden (DE); Adil Duran, Biberach (DE); Peter Eickelmann, Mittelbiberach (DE); Steffen Maier, Biberach (DE); Sabine Pinnetti, Biberach (DE); Regine Ritter, Wiesbaden (DE); Gebhard Schilcher, Mittelbiberach (DE); Ruediger Streicher, Biberach (DE); Leo Thomas, Biberach (DE)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/404,442

(22) Filed: Mar. 16, 2009

(65) Prior Publication Data

US 2009/0181905 A1 Jul. 16, 2009

Related U.S. Application Data

(63) Continuation of application No. 11/621,859, filed on Jan. 10, 2007, now Pat. No. 7,524,822.

(30) Foreign Application Priority Data

Jan. 11, 2006 (EP) .................. 06000483

(51) Int. Cl.
*A01N 43/04* (2006.01)
*A61K 31/70* (2006.01)
(52) U.S. Cl. .............. 514/27; 514/25; 514/26
(58) Field of Classification Search ............... None
See application file for complete search history.

(56) References Cited

U.S. PATENT DOCUMENTS

| | | | |
|---|---|---|---|
| 6,815,428 B2 | 11/2004 | Ohsumi et al. | |
| 6,908,905 B2 | 6/2005 | Ohsumi et al. | |
| 7,015,201 B2 | 3/2006 | Ohsumi et al. | |
| 7,247,616 B2 | 7/2007 | Ohsumi et al. | |
| 7,256,209 B2 | 8/2007 | Ohsumi et al. | |
| 7,375,090 B2 | 5/2008 | Himmelsbach et al. | |
| 7,439,232 B2 | 10/2008 | Kakinuma et al. | |
| 2003/0054453 A1 | 3/2003 | Curtis et al. | |
| 2005/0143424 A1 | 6/2005 | Maezono et al. | |
| 2005/0233982 A1 | 10/2005 | Himmelsbach et al. | |
| 2007/0072813 A1 | 3/2007 | Himmelsbach et al. | |
| 2007/0099979 A1 | 5/2007 | Ohsumi et al. | |
| 2007/0270479 A1 | 11/2007 | Ohsumi et al. | |
| 2007/0281940 A1 | 12/2007 | Dugi | |
| 2008/0020987 A1 | 1/2008 | Pfrengle | |

FOREIGN PATENT DOCUMENTS

| | | |
|---|---|---|
| AU | 2003262262 A1 | 3/2004 |
| CA | 2 494 179 A1 | 2/2004 |
| CA | 2 496 329 A1 | 3/2004 |
| CA | 2 500 873 A1 | 4/2004 |
| CA | 2 507 665 A1 | 6/2004 |
| CA | 2 539 032 A1 | 3/2005 |
| EP | 1 213 296 A1 | 6/2002 |
| EP | 1 338 603 A1 | 8/2003 |
| EP | 1 364 888 A1 | 10/2003 |
| EP | 1 389 621 A1 | 2/2004 |
| EP | 1 400 529 A1 | 3/2004 |
| EP | 1 500 403 A1 | 1/2005 |
| EP | 1 550 668 A1 | 7/2005 |
| EP | 1 609 799 A1 | 12/2005 |
| EP | 1 637 539 A1 | 3/2006 |
| JP | 2003/12686 A1 | 1/2003 |
| WO | 03/020737 A1 | 3/2003 |
| WO | 2004/014932 A1 | 2/2004 |
| WO | 2004/018491 A1 | 3/2004 |
| WO | 2004/019958 A1 | 3/2004 |
| WO | 2004/031203 A1 | 4/2004 |
| WO | 2004/050122 A1 | 6/2004 |
| WO | 2004/089966 A1 | 10/2004 |
| WO | 2004/113359 A1 | 12/2004 |
| WO | 2005/021566 A2 | 3/2005 |
| WO | 2007/010015 A1 | 1/2007 |
| WO | 2007/014895 A1 | 2/2007 |
| WO | 2007/128761 A3 | 11/2007 |

OTHER PUBLICATIONS

D. Giron; Thermal Analysis and Calorimetric Methods in the Characterisation of Polymorphs and Solvates; Thermochimica Acta (1995) vol. 248 pp. 1-59.
Bruce C. Hamper et al; Cyclocondensation of Alkylhydrazines and Beta-Substituted Acetylenic Esters: Synthesis of 3-Hydroxypyrazoles; Journal Organic Chemistry (1992) vol. 57 pp. 5680-5686.
Pyrazolinone Herbicides; Chemical Abstract Service (1981) p. 151890.
C. A. Rojahn; 1-Alkyl-3-Chloropyrazoles and 1-Alkyl-3-Pyrazolones; Chemical Abstract Service (1923) p. 6867.
V. I. Saloutin et al; Study of the Reaction of Fluoroalkyl Beta-Ketoesters with Methylhydrazine; Bulletin of the Academy of Sciences of the USSR (1988) vol. 37 No. 12 pp. 318-321.
Diane Zimmermann et al; Unambiguous Synthesis of 1-Methyl-3-Hydroxypyrazoles; Tetrahedron (1998) vol. 54 No. 32 pp. 9393-9400; Elsevier Science Publishers.

(Continued)

*Primary Examiner*—Patrick T Lewis
(74) *Attorney, Agent, or Firm*—Oblon, Spivak, McClelland, Maier & Neustadt, L.L.P.

(57) ABSTRACT

The invention relates to a crystalline form of 1'-(1-methylethyl)-4'-[(2-fluoro-4-methoxyphenyl)methyl]-5'-methyl-1H-pyrazol-3'-O-β-D-glucopyranoside, to a method for the preparation thereof, as well as to the use thereof for preparing medicaments.

26 Claims, 1 Drawing Sheet

OTHER PUBLICATIONS

International Search Report for PCT/EP2006/064435 mailed Nov. 22, 2006.

International Search Report for PCT/EP2006/064715 mailed Feb. 21, 2007.

International Search Report for PCT/EP2007/050209 mailed Apr. 13, 2007.

Ernest M. Wright et al; The Sodium/Glucose Cotransport Family SLC5; European Journal Renal Physiology (2004) vol. 447 pp. 510-518.

Guofeng You et al; Molecular Characteristics of Na+ -Coupled Glucose Transporters in Adult and Embryonic Rat Kidney; The Journal of Biological Chemistry (1995) vol. 270 No. 49 pp. 29365-29371.

Ana M. Pajor et al; Cloning and Functional Expression of a Mammalian Na+/Nucleoside Cotransporter; The Journal of Biological Chemistry (1992) vol. 267 No. 6 pp. 3557-3560.

Lubing Zhou et al; Human Cardiomyocytes Express High Level of Na+/Glucose Cotransporter 1 (SGLT1); Journal of Cellular Biochemistry (2003) vol. 90 pp. 339-346.

Ana Diez-Sampedro et al; A Glucose Sensor Hiding in a Family of Transporters; The National Academey of Sciences of the USA (2003) vol. 100 No. 20 pp. 11753-11758.

Niloofar M.Tabatabai et al; Mouse Kidney Express mRNA of Four Highly Related Sodium-Glucose Cotransporters: Regulation by Cadmium; Kidney International (2003) vol. 64 pp. 1320-1330.

Walter L. Gouvea et al; Phlorizin-Induced Glycosuria Does Not Prevent Gentamicin Nephrotoxicity in Rats; Kidney International (1989) vol. 35 pp. 1041-1048.

Ernerst M. Wright; Renal Na+ -Glucose Cotransporters; American Journal Physiological Renal Physiological (2001) vol. 280 pp. F10-F18.

James I. Cleeman et al; Executive Summary of the Third Report of the National Cholesterol Education Program (NCEP) Expert Panel on Detection, Evaluation, and Treatment of High Blood Cholesterol in Adults (Adult Treatment Panel III); Journal of the American Medical Association (2001) vol. 285 No. 19 pp. 2486-2497.

International Search Report for PCT/EP2006/064715 mailed on Feb. 21, 2007.

European Search Report for EP 05 01 6390 mailed on May 30, 2006.

Luciano Rossetti et al; Correction of Hyperglycemia with Phlorizin Normalizes Tissue Sensitivity to Insulin in Diabetic Rats; Journal Clinical Investigation (1987) vol. 79 pp. 1510-1515.

U.S. Appl. No. 11/490,426, filed Jul. 20, 2006.

U.S. Appl. No. 11/744,703, filed May 4, 2007.

Expert Panel on Detection, Evaluation, and Treatment of High Blood Cholesterol in Adults, "Executive Summary of the Third Report of the National Cholesterol Education Program (NCEP) Expert Panel on Detection, Evaluation, and Treatment of High Blood Cholesterol in Adults (Adult Treatment Panel III)", JAMA, 2001, vol. 285, No. 13, p. 2486.

M. Stumvoll, et al., "The OGTT as test for beta cell function?", European Journal of Clinical Investigation, 2001, vol. 31, p. 380-381.

American Diabetes Association and National Institute of Diabetes, Digestive and Kidney Diseases, The Prevention or Delay of Type 2 Diabetes, Diabetes Care, 2002, vol. 25, No. 4, p. 742.

A. Katsuki, et al., "Homeostasis Model Assessment is a Reliable Indicator of Insulin Resistance During Follow-up of Patients with Type 2 Diabetes", Diabetes Care, 2001, vol. 24, No. 2, p. 362.

James B. Meigs, et al., "The Natural History of Progression from Normal Glucose Tolerance to Type 2 Diabetes in the Baltimore Longitudinal Study of Aging", Diabetes, 2003, vol. 52, p. 1475.

David E Laaksonen, et al "Metabolic syndrome and Development of Diabetes Mellitus Application and Validation of Recently Suggested Definitions of the Metabolic syndrome in a Prospective Cohort Study", American journal of Epidemiology, 2002, vol. 156, No. 11, p. 1070.

Earl S Ford, et al "Prevalence of the Metabolic Syndrome Among US Adults", JAMA, 2002, vol. 287, No. 3, p. 356.

Matthews, et al. "Homeostasis model assessment: insulin resistance and beta-cell function from fasting plasma glucose and insulin concentrations in man", Diabetologia, 1985, vol. 28, p. 412-419.

Galvin, et al "A Simple method for Quantitation of insulin Sensitivity and Insulin Release from an Intravenous Glucose Tolerance Test", Diabetic Medicine, 1992, vol. 9, p. 921-928.

T. Forst, et al. "Fastening Intact Proinsulin is a Highly Specific indicator of Insulin Resistance in Type 2 Diabetes", Diabetes, 2003, 52(Suppl. 1): A459.

Figure 1: X-ray powder diffraction pattern of the crystalline form
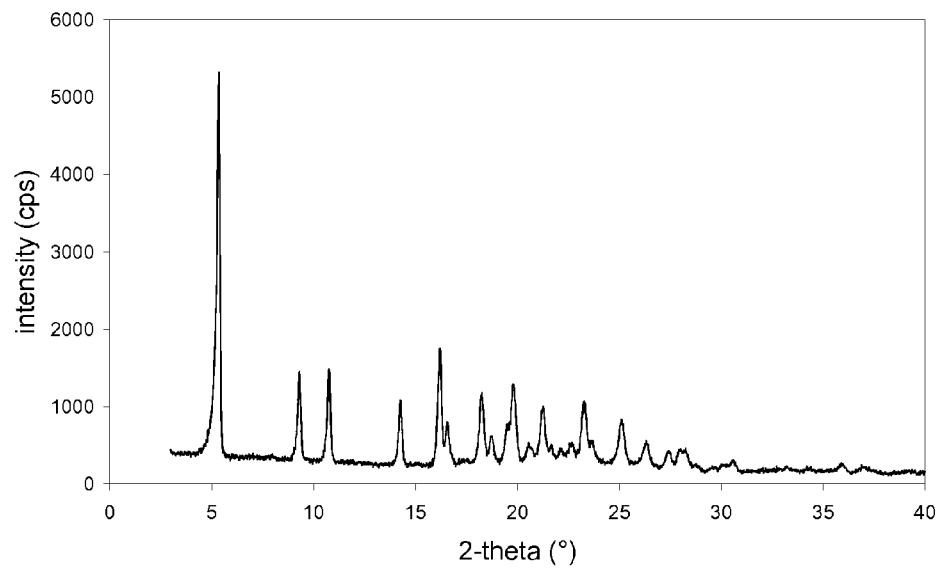
Figure 2: DSC and TG diagram of the crystalline form
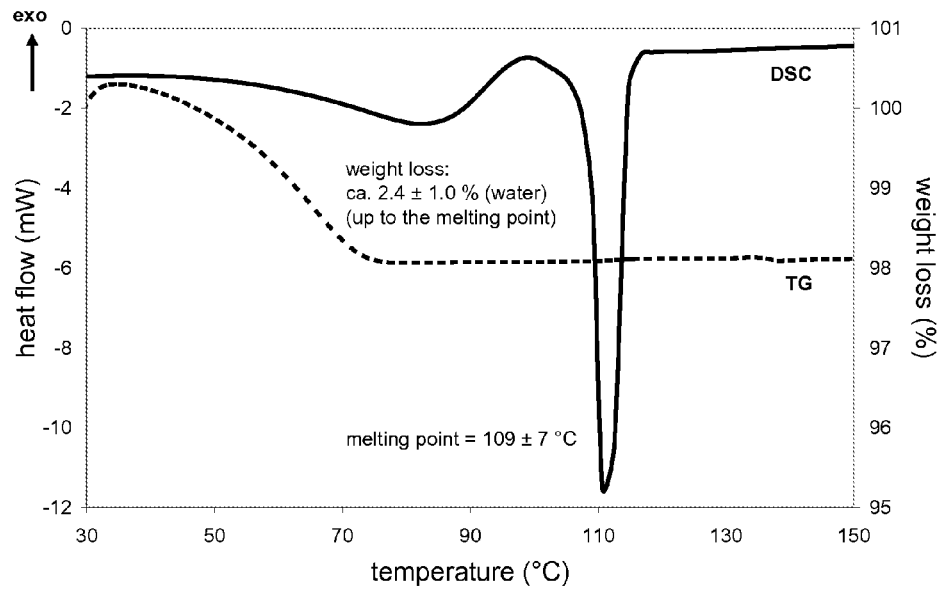

CRYSTALLINE FORM OF 1'-(1-METHYLETHYL)-4'-[(2-FLUORO-4-METHOXYPHENYL)METHYL]-5'-METHYL-1H-PYRAZOL-3'-O-β-D-GLUCOPYRANOSIDE, A METHOD FOR ITS PREPARATION AND THE USE THEREOF FOR PREPARING MEDICAMENTS

This application is a continuation of U.S. patent application Ser. No. 11/621,859, filed Jan. 10, 2007, and claims priority benefit to EP 06 000 483, filed Jan. 11, 2006, the contents of which are incorporated herein by reference in their entireties.

The invention relates to a crystalline form of 1'-(1-methylethyl)-4'-[(2-fluoro-4-methoxyphenyl)methyl]-5'-methyl-1H-pyrazol-3'-O-β-D-glucopyranoside, to pharmaceutical compositions and to uses of said crystalline form in the therapeutic treatment or prevention. Furthermore the present invention relates to methods for the preparation of such a crystalline form.

BACKGROUND OF THE INVENTION

The compound 1'-(1-methylethyl)-4'-[(2-fluoro-4-methoxyphenyl)methyl]-5'-methyl-1H-pyrazol-3'-O-β-D-glucopyranoside of the formula I

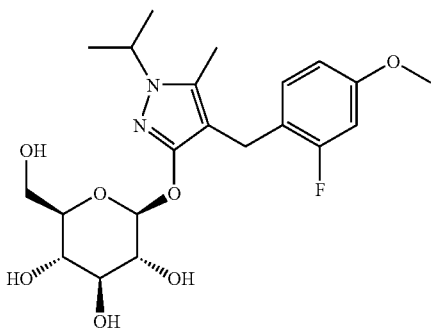

I (in the following referred to it as "compound of the formula I") is described in the European Patent application EP 1338603 A, the contents of which are incorporated herein, and has a valuable inhibitory effect on the sodium-dependent glucose cotransporter SGLT, particularly SGLT2. The method of manufacture of the compound of the formula I as described therein does not yield a crystalline form.

A certain pharmaceutical activity is of course the basic prerequisite to be fulfilled by a pharmaceutically active agent before same is approved as a medicament on the market. However, there are a variety of additional requirements a pharmaceutically active agent has to comply with. These requirements are based on various parameters which are connected with the nature of the active substance itself. Without being restrictive, examples of these parameters are the stability of the active agent under various environmental conditions, its stability during production of the pharmaceutical formulation and the stability of the active agent in the final medicament compositions. The pharmaceutically active substance used for preparing the pharmaceutical compositions should be as pure as possible and its stability in long-term storage must be guaranteed under various environmental conditions. This is essential to prevent the use of pharmaceutical compositions which contain, in addition to the actual active substance, breakdown products thereof, for example. In such cases the content of active substance in the medicament might be less than that specified.

Uniform distribution of the medicament in the formulation is a critical factor, particularly when the medicament has to be given in low doses. To ensure uniform distribution, the particle size of the active substance can be reduced to a suitable level, e.g. by grinding. Since breakdown of the pharmaceutically active substance as a side effect of the grinding (or micronising) has to be avoided as far as possible, in spite of the hard conditions required during the process, it is essential that the active substance should be highly stable throughout the grinding process. Only if the active substance is sufficiently stable during the grinding process it is possible to produce a homogeneous pharmaceutical formulation which always contains the specified amount of active substance in a reproducible manner.

Another problem which may arise in the grinding process for preparing the desired pharmaceutical formulation is the input of energy caused by this process and the stress on the surface of the crystals. This may in certain circumstances lead to polymorphous changes, to amorphization or to a change in the crystal lattice. Since the pharmaceutical quality of a pharmaceutical formulation requires that the active substance should always have the same crystalline morphology, the stability and properties of the crystalline active substance are subject to stringent requirements from this point of view as well.

The stability of a pharmaceutically active substance is also important in pharmaceutical compositions for determining the shelf life of the particular medicament; the shelf life is the length of time during which the medicament can be administered without any risk. High stability of a medicament in the abovementioned pharmaceutical compositions under various storage conditions is therefore an additional advantage for both the patient and the manufacturer.

The absorption of moisture reduces the content of pharmaceutically active substance as a result of the increased weight caused by the uptake of water. Pharmaceutical compositions with a tendency to absorb moisture have to be protected from moisture during storage, e.g. by the addition of suitable drying agents or by storing the drug in an environment where it is protected from moisture. Preferably, therefore, a pharmaceutically active substance should be only slightly hygroscopic.

Furthermore, the availability of a well-defined crystalline form allows the purification of the drug substance by recrystallization.

Apart from the requirements indicated above, it should be generally borne in mind that any change to the solid state of a pharmaceutical composition which is capable of improving its physical and chemical stability gives a significant advantage over less stable forms of the same medicament.

The aim of the invention is thus to provide a new, stable crystalline form of the compound of the formula I which meets important requirements imposed on pharmaceutically active substances as mentioned above.

OBJECT OF THE INVENTION

In a first aspect the present invention relates to a crystalline form of the compound of the formula I.

In a second aspect the present invention relates to the crystalline form of the compound of the formula I having an X-ray powder diffraction pattern that comprises peaks at 5.35, 10.76 and 16.20 degrees 2Θ (±0.1 degrees 2Θ), wherein said X-ray powder diffraction pattern is made using CuK$_{\alpha 1}$ radiation.

In a third aspect the present invention relates to the compound of the formula I wherein at least 50% of said substance is present in the form of a crystalline form as defined hereinbefore and hereinafter.

In a fourth aspect the present invention relates to a pharmaceutical composition or medicament comprising a crystalline form as defined hereinbefore and hereinafter.

In a fifth aspect the present invention relates to a use of a crystalline form as defined hereinbefore or hereinafter for preparing a pharmaceutical composition for inhibiting the sodium-dependent glucose cotransporter SGLT2.

In a sixth aspect the present invention relates to a use of a crystalline form as defined hereinbefore or hereinafter for preparing a pharmaceutical composition which is suitable for the treatment or prevention of diseases or conditions which can be influenced by inhibiting sodium-dependent glucose cotransporter SGLT, preferably SGLT2.

In a further aspect the present invention relates to a use of a crystalline form as defined hereinbefore or hereinafter for preparing a pharmaceutical composition for preventing, slowing progression of, delaying or treating a metabolic disorder selected from the group consisting of type 1 diabetes mellitus, type 2 diabetes mellitus, impaired glucose tolerance, hyperglycemia, postprandial hyperglycemia, overweight, obesity, including class I obesity, class II obesity, class III obesity, visceral obesity and abdominal obesity, and metabolic syndrome in a patient in need thereof.

In a further aspect the present invention relates to a use of a crystalline form as defined hereinbefore or hereinafter for preparing a pharmaceutical composition for improving glycemic control and/or for reducing of fasting plasma glucose, of postprandial plasma glucose and/or of glycosylated hemoglobin HbA1c in a patient in need thereof.

In a further aspect the present invention relates to a use of a crystalline form as defined hereinbefore or hereinafter for preparing a pharmaceutical composition for preventing, slowing progression of, delaying or treating of a condition or disorder selected from the group consisting of complications of diabetes mellitus such as cataracts and micro- and macrovascular diseases, such as nephropathy, retinopathy, neuropathy, tissue ischaemia, arteriosclerosis, myocardial infarction, stroke and peripheral arterial occlusive disease, in a patient in need thereof.

In a further aspect the present invention relates to a use of a crystalline form as defined hereinbefore or hereinafter for preparing a pharmaceutical composition for preventing, slowing, delaying or reversing progression from impaired glucose tolerance, insulin resistance and/or from metabolic syndrome to type 2 diabetes mellitus in a patient in need thereof.

In a further aspect the present invention relates to a use of a crystalline form as defined hereinbefore or hereinafter for preparing a pharmaceutical composition for reducing the weight or preventing an increase of the weight or facilitating a reduction of the weight in a patient in need thereof.

In a further aspect the present invention relates to a use of a crystalline form as defined hereinbefore or hereinafter for preparing a pharmaceutical composition for preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion in a patient in need thereof.

In a further aspect the present invention relates to a use of a crystalline form as defined hereinbefore or hereinafter for preparing a pharmaceutical composition for maintaining and/or improving the insulin sensitivity and/or for treating or preventing hyperinsulinemia and/or insulin resistance in a patient in need thereof.

In a further aspect the present invention relates to a use of a crystalline form as defined hereinbefore or hereinafter for preparing a pharmaceutical composition for preventing, slowing, delaying or treating diseases or conditions attributed to an abnormal accumulation of liver fat in a patient in need thereof.

In a further aspect the present invention relates to a method for making a crystalline form as defined hereinbefore and hereinafter, said method comprising the following steps:

(a) dissolving the compound of the formula I in a solvent or a mixture of solvents to form a solution, preferably a saturated, nearly saturated or supersaturated solution, preferably with the proviso that the starting material of said compound of the formula I and/or said solvent or mixture of solvents contain at least an amount of 0.5 mol $H_2O$ per mol of the compound of the formula I;

(b) storing preferably with cooling the solution to precipitate the crystalline form out of solution and thus to yield a suspension;

(c) isolating the precipitate from the suspension; and (d) drying the precipitate optionally until an excess of said solvent or mixture of solvents has been removed.

Yet further aspects of the present invention become apparent to the one skilled in the art from the following detailed description of the invention and the examples.

BRIEF DESCRIPTION OF THE FIGURES

The FIG. 1 shows an X-ray powder diffractogram of the crystalline form according to this invention.

The FIG. 2 shows the thermoanalysis and determination of the melting point via DSC and of the weight loss via TG of the crystalline form.

DETAILED DESCRIPTION OF THE INVENTION

Surprisingly, it has been found that there exists a crystalline form of the compound of the formula I which fulfils important requirements mentioned hereinbefore.

Moreover it has been found that the crystalline form according to this invention meets the stringent requirements mentioned above and thus solves the problem on which the present invention is based. Accordingly the present invention relates to a crystalline form of the compound the formula I.

The crystalline form may be identified and distinguished from other crystalline forms by means of their characteristic X-ray powder diffraction (XRPD) patterns.

The crystalline form is characterised by an X-ray powder diffraction pattern that comprises peaks at 5.35, 10.76 and 16.20 degrees 2Θ (±0.1 degrees 2Θ), wherein said X-ray powder diffraction pattern is made using $CuK_{\alpha 1}$ radiation.

In particular said X-ray powder diffraction pattern comprises peaks at 5.35, 9.31, 10.76, 16.20 and 19.81 degrees 2Θ (±0.1 degrees 2Θ), wherein said X-ray powder diffraction pattern is made using $CuK_{\alpha 1}$ radiation.

In particular said X-ray powder diffraction pattern comprises peaks at 5.35, 9.31, 10.76, 14.27, 16.20, 18.25, 19.81 and 23.27 degrees 2Θ (±0.1 degrees 2Θ), wherein said X-ray powder diffraction pattern is made using $CuK_{\alpha 1}$ radiation.

More specifically, the crystalline form is characterised by an X-ray powder diffraction pattern, made using $CuK_{\alpha 1}$ radiation, which comprises peaks at degrees 2Θ (±0.1 degrees 2Θ) as contained in Table 1.

TABLE 1

X-ray powder diffraction pattern of the crystalline form
(only peaks up to 30° in 2 Θ are listed):

| 2 Θ [°] | d-value [Å] | Intensity I/I₀ [%] |
|---|---|---|
| 5.35 | 16.49 | 100 |
| 9.31 | 9.49 | 27 |
| 10.76 | 8.21 | 29 |
| 14.27 | 6.20 | 20 |
| 16.20 | 5.47 | 33 |
| 16.56 | 5.35 | 15 |
| 18.25 | 4.86 | 22 |
| 18.73 | 4.73 | 12 |
| 19.52 | 4.54 | 15 |
| 19.81 | 4.48 | 24 |
| 20.57 | 4.31 | 10 |
| 21.25 | 4.18 | 19 |
| 21.69 | 4.09 | 9 |
| 22.14 | 4.01 | 8 |
| 22.65 | 3.92 | 10 |
| 23.27 | 3.82 | 20 |
| 23.64 | 3.76 | 10 |
| 25.11 | 3.54 | 15 |
| 26.32 | 3.38 | 10 |
| 27.42 | 3.25 | 8 |

Even more specifically, the crystalline form is characterised by an X-ray powder diffraction pattern, made using $CuK_{\alpha 1}$ radiation, which comprises peaks at degrees 2Θ (±0.1 degrees 2Θ) as shown in FIG. 1.

Furthermore the crystalline form of the compound of the formula I is characterised by a melting point of about 109° C.±7° C. (determined via DSC; evaluated at onset-temperature; heating rate 10 K/min). The obtained DSC curve is shown in FIG. 2.

In a humid environment, in particular at a relative humidity≧30%, the crystalline form of the compound of the formula I shows a weight loss by thermal gravimetry (TG) up to the melting point at approximately 100° C. The observed weight loss indicates that the crystalline form contains water which may be bound by adsorption and/or may be part of the crystalline lattice, i.e. the crystalline form may be present as a crystalline hydrate. The content of water in the crystalline form lies in the range from 0 to 10 weight-%, in particular 0.1 to 8 weight-% and 0.1 to 6.5 weight-% which depends on the relative humidity. At a relative humidity between 30 and 50% (preferably at about 20° C.) the water content is usually in the range between 0.5 and 4.0 weight-%. The water content may be determined by methods well known to the one skilled in the art, for example by thermal gravimetry or by Karl Fischer titration. The dotted line in FIG. 2 depicts a weight loss of between 1.9 and 2.9% of water of a sample stored at a relative humidity between about 30 and 50%. The loss of water is also indicated by the endothermic peak of the solid DSC curve between about 40 and 100° C. in the DSC diagram as shown in FIG. 2.

The X-ray powder diffraction patterns are recorded, within the scope of the present invention, using a STOE-STADI P-diffractometer in transmission mode fitted with a location-sensitive detector (OED) and a Cu-anode as X-ray source (CuKα1 radiation, λ=1.54060 Å, 40 kV, 40 mA). In the Table 1 above the values "2Θ [°]" denote the angle of diffraction in degrees and the values "d [Å]" denote the specified distances in Å between the lattice planes. The intensity shown in the FIG. 1 is given in units of cps (counts per second).

In order to allow for experimental error, the above described 2Θ values should be considered accurate to ±0.1 degrees 2Θ, in particular ±0.05 degrees 2Θ. That is to say, when assessing whether a given sample of crystals of the compound of the formula I is the crystalline form in accordance with the invention, a 2Θ value which is experimentally observed for the sample should be considered identical with a characteristic value described above if it falls within ±0.1 degrees 2Θ of the characteristic value, in particular if it falls within ±0.05 degrees 2Θ of the characteristic value.

The melting points are determined by DSC (Differential Scanning Calorimetry) using a DSC 821 (Mettler Toledo). The weight loss is determined by thermal gravimetry (TG) using a TGA 851 (Mettler Toledo).

A further aspect of the present invention relates to a method for making the crystalline form of the compound of the formula I as defined hereinbefore and hereinafter, said method comprising the following steps:

(a) dissolving the compound of the formula I in a solvent or a mixture of solvents to form a solution, preferably a saturated, nearly saturated or supersaturated solution, with the proviso that said compound of the formula I and/or said solvent or mixture of solvents contain at least an amount of 0.5 mol $H_2O$ per mol of the compound of the formula I;

(b) storing the solution to precipitate the crystalline form out of solution and thus to yield a suspension;

(c) isolating the precipitate from the suspension; and (d) drying the precipitate optionally until any excess of said solvent or mixture of solvents has been removed.

The terms "saturated" or "nearly saturated" or "supersaturated" are related to the starting material of the compound of the formula I as used in step (a). For example a solution which is saturated or nearly saturated with respect to the starting material of the compound of the formula I may be supersaturated with respect to its crystalline form.

Suitable solvents are preferably selected from the group consisting of $C_{1-4}$-alkanols, $C_{4-6}$-cyclic ethers, which may be substituted by $C_{1-3}$-alkyl, $C_{4-8}$-esters, $C_{4-8}$-ketones, acetonitrile, mixtures of two or more of these solvents and mixtures of one or more of these solvents with water.

More preferred solvents are selected from the group consisting of methanol, ethanol, i-propanol, butanol, tetrahydrofuran (THF), 2-methyltetrahydrofuran, 1,4-dioxane, butylacetate, methylisobutylketone (2-methyl-2-pentanone), acetonitrile, mixtures of two or more of these solvents and mixtures of one or more of these solvents with water.

Particularly preferred solvents are selected from the group consisting of ethanol, 1-butanol, tetrahydrofuran, 2-methyltetrahydrofuran, n-butylacetate, methylisobutylketone and mixtures of one or more of such solvents with water.

Water itself may also serve as the only solvent in step (a).

The amount of solvent or mixture of solvents is preferably chosen to obtain a saturated or nearly saturated solution. In case tetrahydrofuran is taken as solvent, the amount of tetrahydrofuran is preferably in the range from about 0.1 L to 1 L of tetrahydrofuran per mol of compound of the formula I; even more preferably in the range from about 0.2 to 0.8 L; most preferably from about 0.25 to 0.6 L per mol of compound of the formula I. In case n-butanol is taken as solvent, the amount of 1-butanol is preferably in the range from about 0.5 L to 10 L of n-butanol per mol of compound of the formula I; even more preferably in the range from about 1 to 6 L per mol of compound of the formula I.

The starting material of the compound of the formula I and/or the solvent and mixtures of solvents preferably contain at least an amount of 0.5 mol $H_2O$ per mol of the compound of the formula I; in particular at least 0.5 to 0.7 mol of water per mol of compound of the formula I. Preferably the amount of water is in the range from about 0.5 to 10.0 mol of water per mol of compound of the formula I; even more preferably in the range from about 1 to 8 mol of water per mol of compound of the formula I; most preferably in the range from about 2 to 6 mol of water per mol of compound of the formula I, for example about 4 mol of water. This means that either the compound of the formula I as starting material or said solvent or mixture of solvents, or the compound of the formula I together with said solvent or mixture of solvents contain an amount of $H_2O$ as specified above. For example if the starting material of the compound of the formula I in step (a) does contain sufficient water as specified above, a water content of the solvent(s) is not mandatory.

Preferably the solvent or mixture of solvents (other than water) are added to the compound of the formula I (or vice versa) to yield a solution and then the amount of water is added.

The amount of water in the solvent or mixture of solvents is advantageously at least 0.4 weight-% of the solvent or mixture of solvents, more preferably at least 0.7 weight-% of the solvent or mixture of solvents. According to a preferred example the amount of water is in the range from 0.7 to 0.9 weight-% of the solvent or mixture of solvents.

Preferably the step (a) is carried at about room temperature (about 20° C.) or at an elevated temperature up to about the boiling point of the solvent or mixture of solvents used. A preferred temperature range is between about 35° C. and 100° C., even more preferably from about 45° C. to 80° C.

In step (b) the solution is stored for a time sufficient to obtain a precipitate. The temperature of the solution in step (b) is preferably about the same as or lower than in step (a). During storage the temperature of the solution containing the compound of the formula I is preferably lowered, preferably to a temperature in the range from −10° C. to 25° C. or even lower, even more preferably in the range from −5 to 15° C. Step (b) can be carried out with or without stirring. As known to the one skilled in the art by varying the period of time and the difference of temperature in step (b) the size, shape and quality of the obtained crystals can be controlled. Furthermore the crystallization may be induced by methods known in the art, for example by mechanical means such as scratching or rubbing the contact surface of the reaction vessel with e.g. a glass rod. Optionally the saturated or supersaturated solution may be inoculated with seed crystals.

In order to reduce the solubility of the compound of the formula I in the solution, in step (a) and/or in step (b) one or more antisolvents may be added, preferably during step (a) or at the beginning of step (b). Suitable antisolvents may be selected from the group consisting of ethers, alkanes, cycloalkanes and mixtures thereof, in particular $C_{4-6}$-aliphatic ethers, $C_{6-8}$-alkanes, $C_{6-8}$-cycloalkanes and mixtures thereof. Examples of antisolvents or non-solvents are diisopropylether, tert-butylmethylether (TBME), cyclohexane, methylcyclohexane, hexane, heptane, octane and mixtures thereof, preferably n-heptane or tert-butylmethylether (TBME).

The amount of antisolvent is preferably chosen to obtain a supersaturated or nearly supersaturated solution. In case TBME is taken as an antisolvent, the amount of TBME is preferably in the range from about 2 L to 20 L of TBME per liter of solvent, in particular of THF as solvent; even more preferably in the range from about 4 to 15 L; most preferably from about 5 to 10 L per liter of solvent, in particular of THF as solvent. In case n-heptane is taken as an antisolvent, the amount of n-heptane is preferably in the range from about 0.5 L to 15 L of n-heptane per liter of solvent, in particular of 1-butanol as solvent; even more preferably in the range from about 1 to 10 L; most preferably from about 2 to 6 L per liter of solvent, in particular of 1-butanol as solvent.

In step (c) the solvent(s) can be removed from the precipitate by known methods as for example filtration, suction filtration, decantation or centrifugation.

In step (d) an excess of the solvent(s) is optionally removed from the precipitate by methods known to the one skilled in the art as for example by reducing the partial pressure of the solvent(s), preferably in vacuum, and/or by heating from above room temperature (ca. 20° C.), preferably in a temperature range below 70° C., even more preferably below 50° C., for example between about 35 and 50° C.

During the drying process at elevated temperatures, for example at temperatures of about 30° C. or above, at least some amount of water bound (for example by adsorption) in the crystalline form may also be removed. This process is reversible. Storing of the substance at normal conditions, for example at room temperature (approx. 20° C.) and a relative humidity of 30 to 60%, preferably in a humid environment, for example at a relative humidity of equal to or greater than 80%, yields a higher water content again.

The compound of the formula I may be synthesized by methods as specifically and/or generally described or cited in the European patent application EP 1338603A. Furthermore the biological properties of the compound of the formula I may be investigated as it is described in said European patent application.

A crystalline form in accordance with the invention is preferably employed as drug active substance in substantially pure form, that is to say, essentially free of other crystalline forms of the compound of the formula I. Nevertheless, the invention also embraces the crystalline form according to this invention in admixture with another crystalline form or forms. Should the drug active substance be a mixture of crystalline forms, it is preferred that the substance comprises at least 50% of the crystalline form as described herein.

In view of the ability to inhibit the SGLT activity, a crystalline form according to the invention is suitable for the preparation of pharmaceutical compositions for the treatment and/or preventative treatment of all those conditions or diseases which may be affected by the inhibition of the SGLT activity, particularly the SGLT-2 activity, for example for the treatment and/or preventive treatment of one or more metabolic disorders.

Therefore, a crystalline form according to this invention is particularly suitable for the preparation of pharmaceutical compositions for preventing, slowing progression of, delaying or treating a metabolic disorder selected from the group consisting of type 1 diabetes mellitus, type 2 diabetes mellitus, impaired glucose tolerance, hyperglycemia, postprandial hyperglycemia, overweight, obesity, including class I obesity, class II obesity, class III obesity, visceral obesity and abdominal obesity, and metabolic syndrome in a patient in need thereof.

Furthermore a crystalline form according to this invention is particularly suitable for the preparation of pharmaceutical compositions for improving glycemic control and/or for reducing of fasting plasma glucose, of postprandial plasma glucose and/or of glycosylated hemoglobin HbA1c in a patient in need thereof.

As by a use of the crystalline form according to this invention an improvement of the glycemic control in patients in need thereof is obtainable, also those conditions and/or diseases related to or caused by an increased blood glucose level may be treated.

Therefore a crystalline form according to this invention is particularly suitable for the preparation of pharmaceutical compositions for preventing, slowing progression of, delaying or treating of a condition or disorder selected from the group consisting of complications of diabetes mellitus such as cataracts and micro- and macrovascular diseases, such as nephropathy, retinopathy, neuropathy, tissue ischaemia, arteriosclerosis, myocardial infarction, stroke and peripheral arterial occlusive disease, in a patient in need thereof. The term "tissue ischaemia" particularly comprises diabetic macroangiopathy, diabetic microangiopathy, impaired wound healing and diabetic ulcer.

A crystalline form according to this invention may also have valuable disease-modifying properties with respect to diseases or conditions related to impaired glucose tolerance, insulin resistance and/or metabolic syndrome.

Therefore in another aspect a crystalline form according to this invention is particularly suitable for the preparation of pharmaceutical compositions for preventing, slowing, delaying or reversing progression from impaired glucose tolerance, insulin resistance and/or from metabolic syndrome to type 2 diabetes mellitus in a patient in need thereof.

By the administration of a pharmaceutical composition according to this invention excessive blood glucose levels are not converted to insoluble storage forms, like fat, but excreted through the urine of the patient. Therefore no gain in weight or even a reduction of the weight is the result.

Following this a crystalline form according to this invention is also particularly suitable for the preparation of pharmaceutical compositions for reducing the weight or preventing an increase of the weight or facilitating a reduction of the weight in a patient in need thereof.

The pharmacological effect of a crystalline form according to this invention is independent of insulin. Therefore an improvement of the glycemic control is possible without an additional strain on the pancreatic beta cells. By an administration of a pharmaceutical composition according to this invention a beta-cell degeneration and a decline of beta-cell functionality such as for example apoptosis or necrosis of pancreatic beta cells can be delayed or prevented. Furthermore the functionality of pancreatic cells can be improved or restored, and the number and size of pancreatic beta cells increased. It may be shown that the differentiation status and hyperplasia of pancreatic beta-cells disturbed by hyperglycemia can be normalized by treatment with a pharmaceutical composition according to this invention.

Therefore a crystalline form according to this invention is particularly suitable for the preparation of pharmaceutical compositions for preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion in a patient in need thereof.

As a result a crystalline form according to this invention is particularly suitable for the preparation of pharmaceutical compositions for maintaining and/or improving the insulin sensitivity and/or for treating or preventing hyperinsulinemia and/or insulin resistance in a patient in need thereof.

By the administration of a crystalline form according to this invention an abnormal accumulation of fat in the liver may be reduced or inhibited. Therefore according to another aspect of the present invention there is provided a method for preventing, slowing, delaying or treating diseases or conditions attributed to an abnormal accumulation of liver fat in a patient in need thereof characterized in that a pharmaceutical composition according to this invention is administered. Diseases or conditions which are attributed to an abnormal accumulation of liver fat are particularly selected from the group consisting of general fatty liver, non-alcoholic fatty liver (NAFL), non-alcoholic steatohepatitis (NASH), hyperalimentation-induced fatty liver, diabetic fatty liver, alcoholic-induced fatty liver or toxic fatty liver.

In particular, a crystalline form according to the invention is suitable for the preparation of pharmaceutical compositions for the prevention or treatment of diabetes, particularly type 1 and type 2 diabetes mellitus, and/or diabetic complications.

When this invention refers to patients requiring treatment or prevention, it relates primarily to treatment and prevention in humans, but the crystalline form may also be used accordingly in veterinary medicine on mammals.

Within the scope of the present invention the pharmaceutical composition comprising a crystalline form according to this invention is preferably administered orally. Other forms of administration are possible and described hereinafter. Furthermore the treatment and/or prophylaxis, in the following called therapy, according to this invention is preferably a monotherapy, i.e. during the time of the therapy preferably no other antidiabetic drug other than the crystalline form according to this invention is given to the patient.

As described hereinbefore by the administration of a pharmaceutical composition according to this invention excessive blood glucose is excreted through the urine of the patient, so that no gain in weight or even a reduction of the weight may result. Therefore a treatment or prophylaxis according to this invention is advantageously suitable in those patients in need of such treatment or prophylaxis who are diagnosed of one or more of the conditions selected from the group consisting of overweight, class I obesity, class II obesity, class III obesity, visceral obesity and abdominal obesity or for those individuals in which a weight increase is contraindicated.

It is found that the crystalline form according to this invention exhibits a very good efficacy with regard to glycemic control, in particular in view of a reduction of fasting plasma glucose, postprandial plasma glucose and/or glycosylated hemoglobin (HbA1c). By administering a pharmaceutical composition according to this invention a reduction of HbA1c equal to or greater than preferably 0.5%, even more preferably equal to or greater than 1.0% can be achieved and the reduction is particularly in the range from 1.0% to 1.5%.

Furthermore the methods according to this invention is advantageously applicable in those patients who show one, two or more of the following conditions:
(a) a fasting blood glucose or serum glucose concentration greater than 110 mg/dL, in particular greater than 125 mg/dL;
(b) a postprandial plasma glucose equal to or greater than 140 mg/dL;
(c) an HbA1c value equal to or greater than 6.5%, in particular equal to or greater than 8.0

The present invention also discloses the use of a pharmaceutical composition according to this invention for improving glycemic control in patients having type 2 diabetes or showing first signs of prediabetes. Thus, the invention also includes diabetes prevention. If therefore a pharmaceutical composition according to this invention is used immediately to improve the glycemic control as soon as one of the above-mentioned signs of prediabetes is present, the onset of manifest type 2 diabetes mellitus can be delayed or prevented.

Furthermore a pharmaceutical composition according to this invention is particularly suitable in the treatment of patients with insulin dependency, i.e. in patients who are treated or otherwise would be treated or need treatment with an insulin or a derivative of insulin or a substitute of insulin or a formulation comprising an insulin or a derivative or substitute thereof. These patients include patients with diabetes type 2 and patients with diabetes type 1.

It can be found that by using a pharmaceutical composition according to this invention an improvement of the glycemic control can be achieved even in those patients who have insufficient glycemic control in particular despite treatment with one or more antidiabetic drugs, for example despite maximal tolerated dose of oral monotherapy with either metformin or an antidiabetic of the class of sulphonylureas. A maximal tolerated dose with regard to metformin is for example 850 mg three times a day or any equivalent thereof. In the scope of the present invention the term "insufficient glycemic control" means a condition wherein patients show HbA1c values above 6.5%, in particular above 8%.

Therefore according to a preferred embodiment of the present invention there is provided a method for improving glycemic control and/or for reducing of fasting plasma glucose, of postprandial plasma glucose and/or of glycosylated hemoglobin HbA1c in a patient in need thereof who is diagnosed with impaired glucose tolerance, with insulin resistance, with metabolic syndrome and/or with type 2 or type 1 diabetes mellitus characterized in that a pharmaceutical composition comprising a crystalline form according to this invention is administered.

It is found that the lowering of the blood glucose level by the administration of a pharmaceutical composition according to this invention is insulin-independent. Therefore a crystalline form according to this invention is particularly suitable in the treatment of patients who are diagnosed having one or more of the following conditions insulin resistance,
hyperinsulinemia,
pre-diabetes,
type 2 diabetes mellitus, particular having a late stage type 2 diabetes mellitus,
type 1 diabetes mellitus.

Furthermore a pharmaceutical composition according to this invention is particularly suitable in the treatment of patients who are diagnosed having one or more of the following conditions
(a) obesity (including class I, II and/or III obesity), visceral obesity and/or abdominal obesity,
(b) triglyceride blood level≧150 mg/dL,
(c) HDL-cholesterol blood level<40 mg/dL in female patients and <50 mg/dL in male patients,
(d) a systolic blood pressure≧130 mm Hg and a diastolic blood pressure≧85 mm Hg,
(e) a fasting blood glucose level≧110 mg/dL.

It is assumed that patients diagnosed with impaired glucose tolerance, with insulin resistance and/or with metabolic syndrome suffer from an increased risk of developing a cardiovascular disease, such as for example myocardial infarction, coronary heart disease, heart insufficiency, thromboembolic events. A glycemic control according to this invention may result in a reduction of the cardiovascular risks.

A pharmaceutical composition according to this invention exhibits a good safety profile. Therefore a treatment or prophylaxis according to this invention is advantageous possible in those patients for which the treatment with other antidiabetic drugs, such as for example metformin, is contraindicated and/or who have an intolerance against such drugs at therapeutic doses. In particular a treatment or prophylaxis according to this invention is advantageous possible in those patients showing or having an increased risk for one or more of the following disorders: renal insufficiency or diseases, cardiac diseases, cardiac failure, hepatic diseases, pulmonal diseases, catabolytic states and/or danger of lactate acidosis, or female patients being pregnant or during lactation.

Furthermore it can be found that the administration of a pharmaceutical composition according to this invention results in no or in a low risk of hypoglycemia. Therefore a treatment or prophylaxis according to this invention is also advantageously possible in those patients showing or having an increased risk for hypoglycemia.

The pharmaceutical composition according to this invention is particularly suitable in the long term treatment or prophylaxis of the diseases and/or conditions as described hereinbefore and hereinafter, in particular in the long term glycemic control in patients with type 2 diabetes mellitus.

The term "long term" as used hereinbefore and hereinafter indicates a treatment of or administration in a patient within a period of time longer than 12 weeks, preferably longer than 25 weeks, even more preferably longer than 1 year.

Therefore a particularly preferred embodiment of the present invention provides a method for oral therapy, preferably oral monotherapy, for improvement, especially long term improvement, of glycemic control in patients with type 2 diabetes mellitus, especially in patients with late stage type 2 diabetes mellitus, in particular in patients additionally diagnosed of overweight, obesity (including class I, class II and/or class III obesity), visceral obesity and/or abdominal obesity.

It will be appreciated that the amount of the crystalline form according to this invention to be administered to the patient and required for use in treatment or prophylaxis according to the present invention will vary with the route of administration, the nature and severity of the condition for which treatment or prophylaxis is required, the age, weight and condition of the patient, concomitant medication and will be ultimately at the discretion of the attendant physician. In general however the crystalline form according to this invention is included in the pharmaceutical composition or dosage form in an amount sufficient to improve glycemic control in the patient to be treated.

The pharmaceutical composition to be administered to the patient according to a method as described hereinbefore and hereinafter preferably comprises an amount in the range from 1 mg to 1000 mg, even more preferably from 10 to 500 mg, most preferably from 50 to 500 mg of a crystalline form according to this invention per day with respect to an adult patient. The above specified amounts are especially preferred for oral administration. An example of a suitable pharmaceutical composition according to this invention is a tablet for oral administration comprising 200 mg of a crystalline form according to this invention.

The desired dose of the pharmaceutical composition according to this invention may conveniently be presented in a single dose once daily or as divided dose administered at appropriate intervals, for example as two, three or more doses per day.

The pharmaceutical composition is advantageously formulated for oral administration in solid form. The formulations may, where appropriate, be conveniently presented in discrete dosage units and may be prepared by any of the methods well known in the art of pharmacy. All methods include the step of bringing into association the active compound with finely divided solid carriers or both and then, if necessary, shaping the product into the desired formulation.

The pharmaceutical composition may be formulated in the form of tablets, granules, fine granules, powders, capsules, caplets, soft capsules, pills, dry syrups, chewable tablets, troches, effervescent tablets, suspension, fast dissolving tablets, oral fast-dispersing tablets, etc.

The pharmaceutical composition preferably comprises one or more pharmaceutical acceptable carriers. Such carriers are preferably "acceptable" in the sense of being compatible with the other ingredients of the formulation and not deleterious to the recipient thereof.

Pharmaceutical compositions suitable for oral administration may conveniently be presented as discrete units such as capsules, including soft gelatin capsules, cachets or tablets each containing a predetermined amount of the active ingredient; as a powder or granules; as a suspension or as an emulsion. Tablets and capsules for oral administration may contain conventional excipients such as binding agents, fillers, lubricants, disintegrants, or wetting agents. The tablets may be coated according to methods well known in the art.

Examples of pharmaceutically acceptable carriers are known to the one skilled in the art.

In the foregoing and in the following the terms as defined hereinafter are used:

The term "body mass index" or "BMI" of a human patient is defined as the weight in kilograms divided by the square of the height in meters, such that BMI has units of $kg/m^2$.

The term "overweight" is defined as the condition wherein the individual has a BMI greater than or 25 $kg/m^2$ and less than 30 $kg/m^2$. The terms "overweight" and "pre-obese" are used interchangeably.

The term "obesity" is defined as the condition wherein the individual has a BMI equal to or greater than 30 $kg/m^2$. According to a WHO definition the term obesity may be categorized as follows: the term "class I obesity" is the condition wherein the BMI is equal to or greater than 30 $kg/m^2$ but lower than 35 $kg/m^2$; the term "class II obesity" is the condition wherein the BMI is equal to or greater than 35 $kg/m^2$ but lower than 40 $kg/m^2$; the term "class III obesity" is the condition wherein the BMI is equal to or greater than 40 $kg/m^2$.

The term "visceral obesity" is defined as the condition wherein a waist-to-hip ratio of greater than or equal to 1.0 in men and 0.8 in women is measured. It defines the risk for insulin resistance and the development of pre-diabetes.

The term "abdominal obesity" is usually defined as the condition wherein the waist circumference is >40 inches or 102 cm in men, and is >35 inches or 94 cm in women. With regard to a Japanese ethnicity or Japanese patients abdominal obesity may be defined as waist circumference≧85 cm in men and ≧90 cm in women (see e.g. investigating committee for the diagnosis of metabolic syndrome in Japan).

The term "euglycemia" is defined as the condition in which a subject has a fasting blood glucose concentration within the normal range, greater than 70 mg/dL (3.89 mmol/L) and less than 110 mg/dL (6.11 mmol/L). The word "fasting" has the usual meaning as a medical term.

The term "hyperglycemia" is defined as the condition in which a subject has a fasting blood glucose concentration above the normal range, greater than 110 mg/dL (6.11 mmol/L). The word "fasting" has the usual meaning as a medical term.

The term "postprandial hyperglycemia" is defined as the condition in which a subject has a 2 hour postprandial blood glucose or serum glucose concentration greater than 200 mg/dL (11.11 mmol/L).

The term "impaired glucose tolerance" or "IGT", is defined as the condition in which a subject has a fasting blood glucose concentration or fasting serum glucose concentration greater than 110 mg/dL and less than 126 mg/dl (7.00 mmol/L), or a 2 hour postprandial blood glucose or serum glucose concentration greater than 140 mg/dl (7.78 mmol/L) and less than 200 mg/dL (11.11 mmol/L). The term impaired glucose tolerance is also intended to apply to the condition of impaired fasting glucose. The abnormal glucose tolerance, i.e. the 2 hour postprandial blood glucose or serum glucose concentration can be measured as the blood sugar level in mg of glucose per dL of plasma 2 hours after taking 75 g of glucose after a fast.

The term "hyperinsulinemia" is defined as the condition in which a subject with insulin resistance, with or without euglycemia, in which the fasting or postprandial serum or plasma insulin concentration is elevated above that of normal, lean individuals without insulin resistance, having a waist-to-hip ration<1.0 (for men) or <0.8 (for women).

The terms "insulin-sensitizing", "insulin resistance-improving" or "insulin resistance-lowering" are synonymous and used interchangeably.

The term "insulin resistance" is defined as a state in which circulating insulin levels in excess of the normal response to a glucose load are required to maintain the euglycemic state (Ford E S, et al. *JAMA*. (2002) 287:356-9). A method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. In this method it is not possible to distinguish between hepatic and peripheral insulin resistance.

Furthermore insulin resistance, the response of a patient with insulin resistance to therapy, insulin sensitivity and hyperinsulinemia may be quantified by assessing the "homeostasis model assessment to insulin resistance (HOMA-IR)" score, a reliable indicator of insulin resistance (Katsuki A, et al. Diabetes Care 2001; 24: 362-5). Further reference is made to methods for the determination of the HOMA-index for insulin sensitivity (Matthews et al., *Diabetologia* 1985, 28:412-19), of the ratio of intact proinsulin to insulin (Forst et al., *Diabetes* 2003, 52(*Suppl*. 1): A459) and to an euglycemic clamp study. In addition, plasma adiponectin levels can be monitored as a potential surrogate of insulin sensitivity. The estimate of insulin resistance by the homeostasis assessment model (HOMA)-IR score is calculated with the formula (Galvin P, et al. Diabet Med 1992; 9:921-8):

$$\text{HOMA-IR}=[\text{fasting serum insulin }(\mu U/mL)] \times [\text{fasting plasma glucose(mmol/L)}/22.5]$$

As a rule, other parameters are used in everyday clinical practice to assess insulin resistance. Preferably, the patient's triglyceride concentration is used, for example, as increased triglyceride levels correlate significantly with the presence of insulin resistance.

Patients with a predisposition for the development of IGT or type 2 diabetes are those having euglycemia with hyperinsulinemia and are by definition, insulin resistant. A typical patient with insulin resistance is usually overweight or obese. If insulin resistance can be detected this is a particularly strong indication of the presence of prediabetes. Thus, it may be that in order to maintain glucose homeostasis a person needs 2-3 times as much insulin as another person, without this having any direct pathological significance.

The methods to investigate the function of pancreatic beta-cells are similar to the above methods with regard to insulin sensitivity, hyperinsulinemia or insulin resistance: An improvement of the beta-cell function can be measured for example by determining a HOMA-index for beta-cell function (Matthews et al., *Diabetologia* 1985, 28:412-19), the ratio of intact proinsulin to insulin (Forst et al., *Diabetes* 2003, 52(*Suppl.* 1): A459), the insulin/C-peptide secretion after an oral glucose tolerance test or a meal tolerance test, or by employing a hyperglycemic clamp study and/or minimal modeling after a frequently sampled intravenous glucose tolerance test (Stumvoll et al., *Eur J Clin Invest* 2001, 31: 380-81).

The term "pre-diabetes" is the condition wherein an individual is pre-disposed to the development of type 2 diabetes. Pre-diabetes extends the definition of impaired glucose tolerance to include individuals with a fasting blood glucose within the high normal range≧100 mg/dL (J. B. Meigs, et al. Diabetes 2003; 52:1475-1484) and fasting hyperinsulinemia (elevated plasma insulin concentration). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

Individuals likely to have insulin resistance are those who have two or more of the following attributes: 1) overweight or obese, 2) high blood pressure, 3) hyperlipidemia, 4) one or more $1^{st}$ degree relative with a diagnosis of IGT or type 2 diabetes. Insulin resistance can be confirmed in these individuals by calculating HOMA-IR score. For the purpose of this invention, insulin resistance is defined as the clinical condition in which an individual has a HOMA-IR score>4.0 or a HOMA-IR score above the upper limit of normal as defined for the laboratory performing the glucose and insulin assays.

The term "type 2 diabetes" is defined as the condition in which a subject has a fasting blood glucose or serum glucose concentration greater than 125 mg/dL (6.94 mmol/L). The measurement of blood glucose values is a standard procedure in routine medical analysis. If a glucose tolerance test is carried out, the blood sugar level of a diabetic will be in excess of 200 mg of glucose per dL of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject the blood sugar level before taking the glucose will be between 60 and 110 mg per dL of plasma, less than 200 mg per dL 1 hour after taking the glucose and less than 140 mg per dL after 2 hours. If after 2 hours the value is between 140 and 200 mg this is regarded as abnormal glucose tolerance.

The term "late stage type 2 diabetes mellitus" includes patients with a secondary drug failure, indication for insulin therapy and progression to micro- and macrovascular complications e.g. diabetic nephropathy, coronary heart disease (CHD).

The term "HbA1c" refers to the product of a non-enzymatic glycation of the haemoglobin B chain. Its determination is well known to one skilled in the art. In monitoring the treatment of diabetes mellitus the HbA1c value is of exceptional importance. As its production depends essentially on the blood sugar level and the life of the erythrocytes, the HbA1c in the sense of a "blood sugar memory" reflects the average blood sugar levels of the preceding 4-6 weeks. Diabetic patients whose HbA1c value is consistently well adjusted by intensive diabetes treatment (i.e. <6.5% of the total haemoglobin in the sample), are significantly better protected against diabetic microangiopathy. For example metformin on its own achieves an average improvement in the HbA1c value in the diabetic of the order of 1.0-1.5%. This reduction of the HbA1C value is not sufficient in all diabetics to achieve the desired target range of <6.5% and preferably <6% HbA1c.

The "metabolic syndrome", also called "syndrome X" (when used in the context of a metabolic disorder), also called the "dysmetabolic syndrome" is a syndrome complex with the cardinal feature being insulin resistance (Laaksonen D E, et al. *Am J Epidemiol* 2002; 156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) *JAMA: Journal of the American Medical Association* (2001) 285:2486-2497), diagnosis of the metabolic syndrome is made when three or more of the following risk factors are present:

1. Abdominal obesity, defined as waist circumference>40 inches or 102 cm in men, and >35 inches or 94 cm in women; or with regard to a Japanese ethnicity or Japanese patients defined as waist circumference≧85 cm in men and ≧90 cm in women;
2. Triglycerides: ≧150 mg/dL
3. HDL-cholesterol<40 mg/dL in men
4. Blood pressure≧130/85 mm Hg (SBP≧130 or DBP≧85)
5. Fasting blood glucose≧110 mg/dL The NCEP definitions have been validated (Laaksonen D E, et al. *Am J Epidemiol*. (2002) 156:1070-7). Triglycerides and HDL cholesterol in the blood can also be determined by standard methods in medical analysis and are described for example in Thomas L (Editor): "Labor und Diagnose", TH-Books Verlagsgesellschaft mbH, Frankfurt/Main, 2000.

According to a commonly used definition hypertension is diagnosed if the systolic blood pressure (SBP) exceeds a value of 140 mm Hg and diastolic blood pressure (DBP) exceeds a value of 90 mm Hg. If a patient is suffering from manifest diabetes it is currently recommended that the systolic blood pressure be reduced to a level below 130 mm Hg and the diastolic blood pressure be lowered to below 80 mm Hg.

The terms "prophylactically treating" and "preventing" are used interchangeably.

The following examples of synthesis serve to illustrate a method of preparing the compound of the formula I and its crystalline form. It is to be regarded only as a possible method described by way of example, without restricting the invention to its contents.

In the foregoing and following text, H atoms of hydroxyl groups are not explicitly shown in every case in structural formulae. In case the pressure is indicated in the unit "bar", the corresponding values can be converted into SI units by using 1 bar=0.1 MPa. In case the pressure is indicated in the unit "psi", the corresponding values can be converted into SI units by using 1 psi=6894.757 Pa. The following abbreviations are used hereinbefore and hereinafter:

TBME tert-butylmethylether,

THF tetrahydrofuran.

EXPERIMENTAL PROCEDURES
Example 1
Synthesis of 1-(1-methylethyl)-4'-[(2-fluoro-4-methoxyphenyl)-methyl]-5'-methyl-1H-pyrazol-3'-O-β-D-glucopyranoside (I)
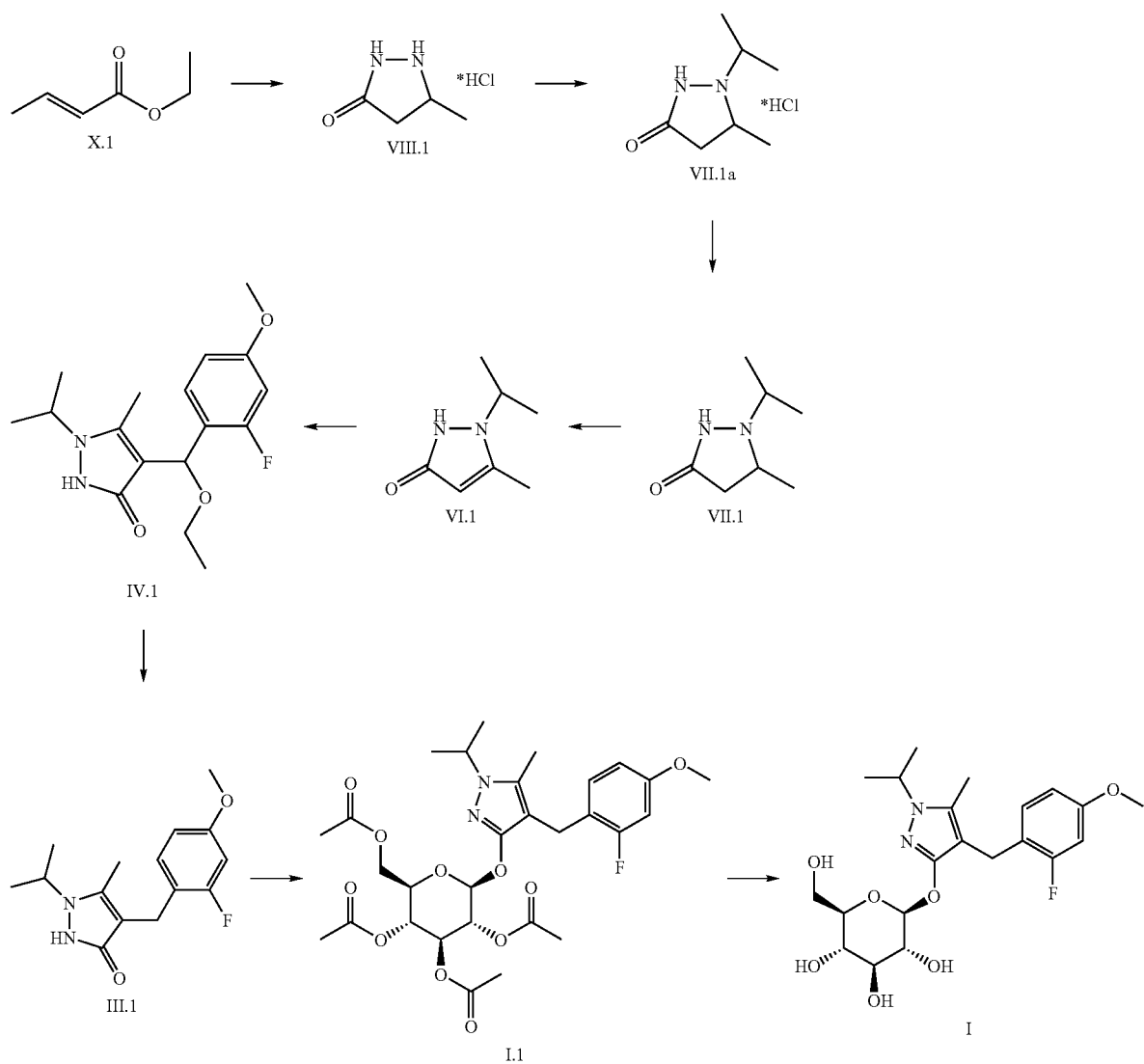
Example 1.1
Preparation of 5-Methyl-3-pyrazolidinone Monohydrochloride (VIII.1)
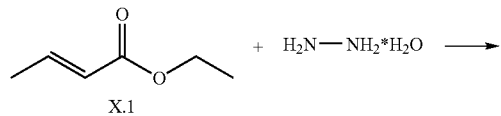
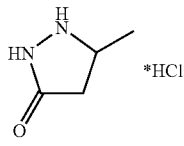
Ethyl crotonate (500 ml; 3.94 mol) is dissolved in isopropanol (1.85 L) and heated to 50° C. Hydrazine hydrate (215 ml; 4.34 mol) is added within 30 min. and the reaction mixture is heated to reflux for 2 h. The solvent is then distilled off (approx. 1 L) under reduced pressure. Isopropanol (400 ml) is then added and the reaction mixture is cooled to 22° C. Hydrochloric acid 11.7 N in ethanol (375 ml, 3.94 mol) is added and the reaction mixture is stirred at about 20 to 25° C. 15 h. The reaction mixture is then cooled to 0° C., filtered and the product is washed with isopropanol (3 times with each 200 ml); then dried to constant weight at 45° C. to yield colorless crystals. Mass and $^1$H-NMR-spectra are in accordance with the assigned structure.

Mass spectrum (ESI$^+$): m/z=101 [M+H]$^+$

Example 1.2

Preparation of 1-(1-Methylethyl)-5-methyl-3-pyrazolidinone Monohydrochloride (VII.1a)

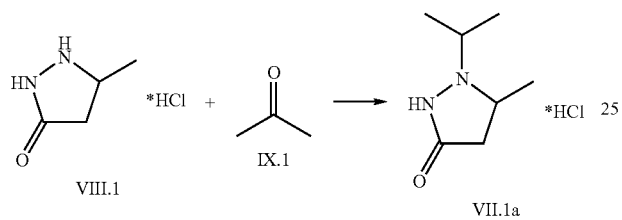

5-Methyl-3-pyrazolidinone monohydrochloride (692 g; 5.07 mol) is suspended in isopropanol (4.9 L). Aqueous 50% sodium hydroxide (270 ml; 5.07 mol) and palladium (10%-weight) on charcoal (70 g) together with acetone (744 ml, 10 mol) are added. The mixture is then hydrogenated under an atmosphere of hydrogen at 50° C. 3 bar (42 psi) until uptake of hydrogen ceases. The reaction mixture is filtered and solvent is distilled off under reduced pressure.

The residue is treated two times with 1 L of isopropanol which is subsequently distilled off under reduced pressure. The remainder is dissolved in isopropanol (3.5 L) and filtered. To the filtrate is added hydrogen chloride 10.5N in ethanol (482 ml; 5.06 mol) which causes the precipitation of the hydrochloride salt which is isolated by filtration. It is washed two times with isopropanol (2×500 ml) and dried at 45° C. to yield the product as colourless crystals. Mass and $^1$H-NMR-spectra are in accordance with the assigned structure.

Mass spectrum (ESI$^+$): m/z=143 [M+H]$^+$

Example 1.3

Preparation of 1-(1-methylethyl)-5-methyl-3-pyrazolidinone (VII.1)

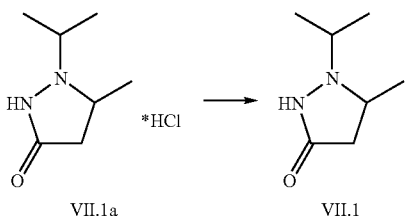

(1-Methylethyl)-5-methyl-3-pyrazolidinone monohydrochloride (150 g; 0.84 mol) is treated with saturated aqueous potassium carbonate (1.2 L) and ethyl acetate (1.0 L). The mixture is filtered and the phases are separated. The organic phase is dried with anhydrous sodium sulphate, filtered and evaporated in vacuo to yield 1-(1-methylethyl)-5-methyl-3-pyrazolidinone as a solid.

Mass and $^1$H-NMR-spectra are in accordance with the assigned structure.

Mass spectrum (ESI$^+$): m/z=143 [M+H]$^+$

Example 1.4

Preparation of 1,2-dihydro-1-(1-methylethyl)-5-methyl-3H-pyrazol-3-one (VI.1)

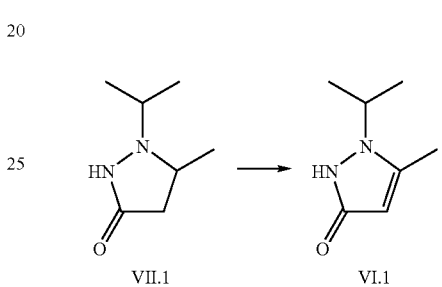

1-(1-methylethyl)-5-methyl-3-pyrazolidinone (390 g; 2.74 mol) is dissolved in acetic acid (170 ml) with warming. 35% aqueous hydrogen peroxide (260 ml; 3.0 mol) is added within 3 h while keeping the temperature at about 65° C. The reaction mixture is then stirred at about 20 to 25° C. for 15 h. Water (1.2 L) is then added and the pH of the mixture is adjusted to about 7 by means of addition of approx. 1 L 50%-weight aqueous sodium hydroxide solution. Upon cooling to 5° C. the reaction mixture is filtered. The product is washed with water and dried at about 50° C. Colourless crystals are obtained.

Mass and $^1$H-NMR-spectra are in accordance with the assigned structure.

Mass spectrum (ESI$^+$): m/z=141 [M+H]$^+$

Example 1.5

1,2-Dihydro-1-(1-methylethyl)-4-[(2-fluor-4-methoxyphenyl)-(ethoxy)methyl]-5-methyl-3H-pyrazol-3-one (IV.1)

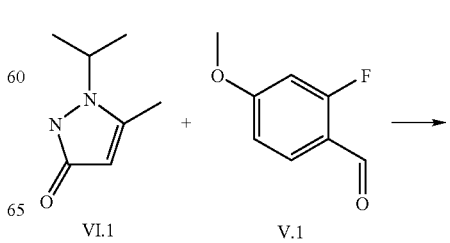

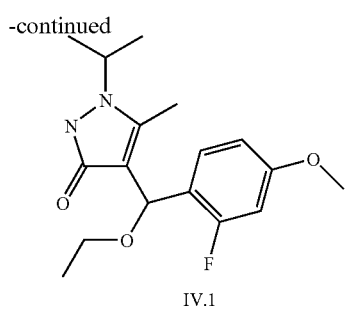

IV.1

Pyrrolidine (21 ml; 0.257 mol) and acetic acid (22 ml; 0.385 mol) are added to a mixture of 1,2-dihydro-1-(1-methylethyl)-5-methyl-3H-pyrazol-3-one (180 g; 1.28 mol) and 2-fluoro-4-methoxybenzaldehyde (198 g; 1.28 mol) in ethanol (2.7 L). The suspension is heated to about 50° C. for about 67 h. The reaction mixture is then cooled to approx. 17° C. and filtered. The product is washed with diisopropyl ether (500 ml) and subsequently refluxed with THF (2.5 L). The obtained solution is filtered over a pad of Celite and charcoal. The filtrate is concentrated in vacuo and water (2 L) is added to the suspension which is cooled and filtered. The colourless crystals are dried at 50° C.

Mass and $^1$H-NMR-spectra are in accordance with the assigned structure.

Mass spectrum (ESI$^+$): m/z=323 [M+H]$^+$

Example 1.6

1,2-Dihydro-1-(1-methylethyl)-4-[(2-fluor-4-methoxyphenyl)methyl]-5-methyl-3H-pyrazol-3-one (III.1)

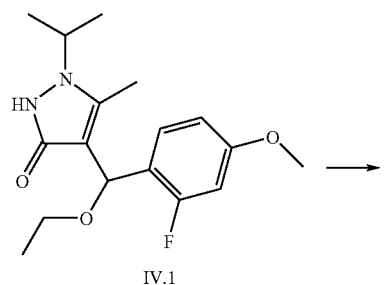

IV.1

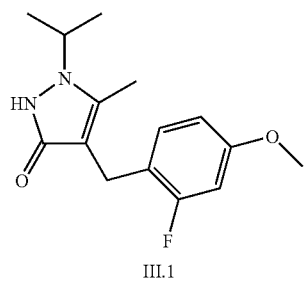

III.1

A mixture of 1,2-dihydro-1-(1-methylethyl)-4-[(2-fluor-4-methoxyphenyl)-(ethoxy)methyl]-5-methyl-3H-pyrazol-3-one (294 g; 1.28 mol), methanol (4.5 L), aqueous hydrochloric acid (30%; 11 g) and water (80 mL) is hydrogenated with palladium on charcoal (10%-weight) (65 g) at 50° C. and 3 bar hydrogen pressure until hydrogen uptake ceases. THF (2.3 L) is added to the reaction mixture which is then filtered. The catalyst is washed with THF (1 L) and the solvent is distilled off under reduced pressure to a residual volume of approx. 700 to 800 ml. The resulting suspension is poured into water (1 L) with stirring. The precipitate is isolated by filtration, washed with water (400 ml) and dried at 55° C. to yield crystals (light beige).

Mass and $^1$H-NMR-spectra are in accordance with the assigned structure.

Mass spectrum (ESI$^+$): m/z=279 [M+H]$^+$

Example 1.7

2,3,4,6-Tetra-O-acetyl-α-D-glucopyranosyl Bromide (II.1)

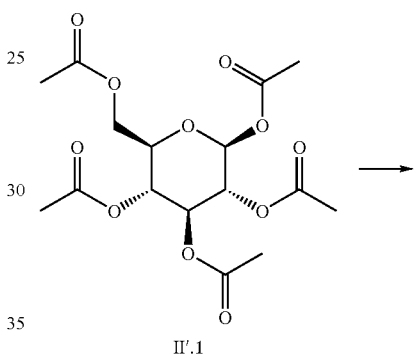

II'.1

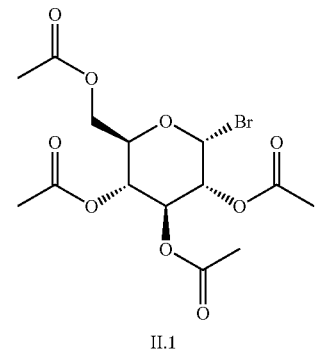

II.1

1,2,3,4,6-Penta-O-acetyl-β-D-glucopyranose (100 g, 0.251 mol) is suspended in toluene (210 ml). Acetic anhydride (9.5 ml; 0.1 mol) is added followed by hydrobromic acid 30% in acetic acid (200 ml, 1 mol). The mixture is stirred at 18° C. for 30 min. A mixture of ice/water (300 ml) and brine (100 ml) is then added with stirring. The phases are separated and the aqueous phase is extracted with toluene (100 ml). The organic phases are combined and washed with aqueous sodium hydrogencarbonate (100 ml) and brine (100 ml). Drying and evaporation of the solvent under reduced pressure yields an oil which is crystallised by addition of methyl-t-butylether (150 ml) and methylcyclohexane (300 ml). The product is isolated by filtration, washed with methylcyclohexane and dried under vacuo at 45° C.

Example 1.8

1'-(1-methylethyl)-4'-[(2-fluoro-4-methoxyphenyl)methyl]-5'-methyl-1H-pyrazol-3'-O-(2,3,4,6-O-tetraacetyl)-β-D-glucopyranoside (I.1)

Examples 1.9a, b

1'-(1-methylethyl)-4'-[(2-fluoro-4-methoxyphenyl)methyl]-5'-methyl-1H-pyrazol-3'-O-β-D-glucopyranoside (I)

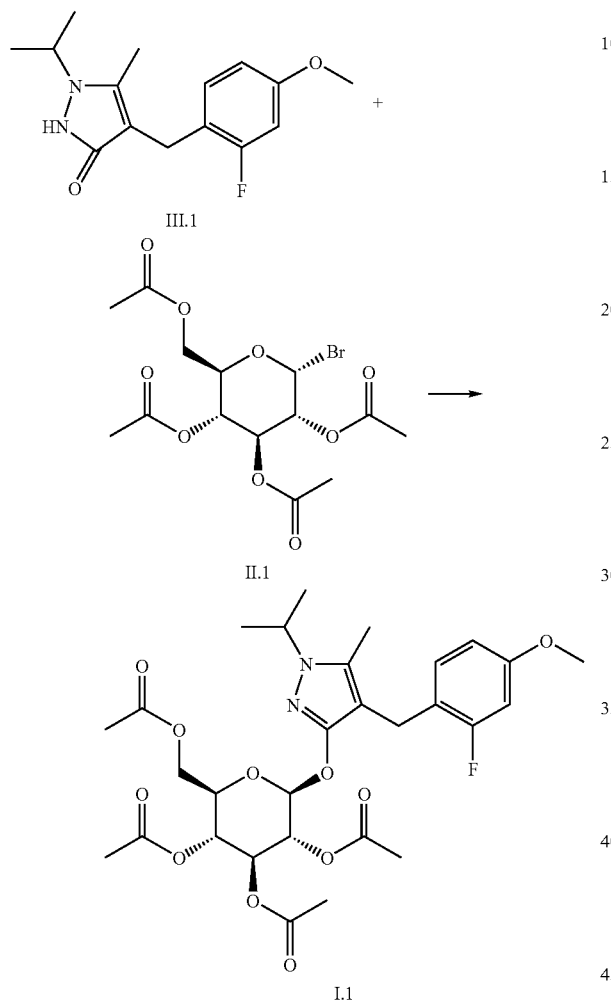

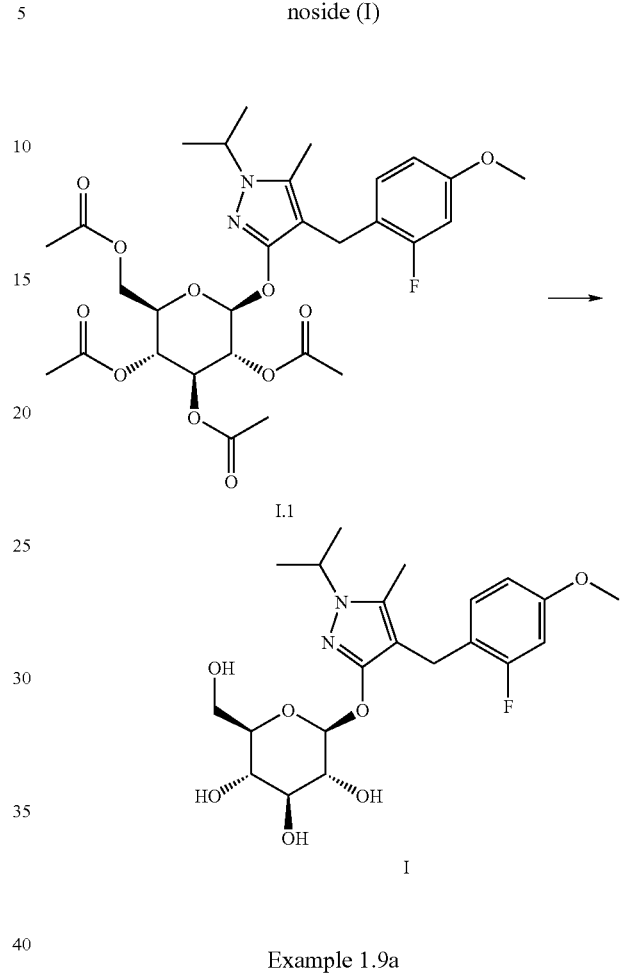

Aqueous potassium hydroxide (1M; 870 ml) is added to a mixture of (2,3,4,6-O-tetraacetyl)-α-D-glucopyranosyl bromide (485 g; 1.169 mol), 1,2-dihydro-1-(1-methylethyl)-4-[(2-fluor-4-methoxyphenyl)methyl]-5-methyl-3H-pyrazol-3-one (161 g; 0.58 mol) and tetrabutylammonium chloride (9.4 g; 0.029 mol) in dichloromethane (780 mL). The two phase mixture is vigorously stirred at 25 to 27° C. while the pH of the aqueous layer is kept constant at approx. 13 by adding further aqueous potassium hydroxide (4N; about 870 ml) until consumption of base ceases (about 5 h). The progress of the reaction can be monitored by HPLC. The phases are then separated and the aqueous phase is extracted with dichloromethane (800 ml). The combined organic phases are dried ($Na_2SO_4$), filtered and evaporated under reduced pressure to yield an oil (yellow). This is used in the next reaction step without further purification.

Mass and $^1$H-NMR-spectra are in accordance with the assigned structure.

Mass spectrum (ESI$^+$): m/z=609 [M+H]$^+$

Example 1.9a

Crude 1'-(1-methylethyl)-4'-[(2-fluoro-4-methoxyphenyl)methyl]-5'-methyl-1H-pyrazol-3'-O-(2,3,4,6-O-tetraacetyl)-β-D-glucopyranoside (413 g; approx. 0.58 mol) of the previous reaction is dissolved in dry ethanol (1 L). Potassium-t-butoxide (6.6 g; 0.058 mol) is then added and the reaction mixture is stirred at about 20 to 25° C. for approx. 15 h. Acetic acid (3.3 ml; 0.058 mol) is then added and the solvent is distilled off under reduced pressure. The resulting residue is then dissolved in ethyl acetate (2 L) and washed with brine (800 ml). The organic phase is separated, dried over $Na_2SO_4$, filtered and evaporated under reduced pressure to yield a resinous solid.

Mass and $^1$H-NMR-spectra are in accordance with the assigned structure.

Mass spectrum (ESI$^+$): m/z=441 [M+H]$^+$

Example 1.9b

Crude 1'-(1-methylethyl)-4'-[(2-fluoro-4-methoxyphenyl)methyl]-5'-methyl-1H-pyrazol-3'-O-(2,3,4,6-O-tetraacetyl)-β-D-glucopyranoside (328 g) of the previous reaction is dissolved in 1-butanol (900 mL). Sodium methoxide, 30% solution in methanol (146 g, 0.808 mol) is then added and the reaction mixture is stirred at about 20 to 25° C. for approx. 15 h. The reaction mixture is washed three times with brine (15%, 600 mL, 300 mL, 300 mL) then 90% of the solvent is removed by distillation under reduced pressure.

Example 2

Preparation of the Crystalline Form

As described hereinbefore during the drying process at elevated temperatures, for example at temperatures of about 50° C. or above, and depending on the conditions during the drying process, like low relative humidity, at least some amount of water may also be removed. As this process is reversible, storing of the substance at normal conditions, preferably in a humid environment, for example at a relative humidity above 30% or between 30 and 60%, increases the water content again.

Example 2.1

21.9 g of resinous or foamy 4'-[(2-fluoro-4-methoxyphenyl)methyl]-5'-methyl-1'-(1-methylethyl)-1H-pyrazol-3'-O-β-D-glucopyranoside is dissolved in ethanol. The solvent is distilled off under reduced pressure just to the point of beginning of foaming. The resulting thick, clear syrup is dissolved in water (75 ml) at about 20° C. and crystallisation is induced by scratching with a glass rod. The process of crystallisation is completed by stirring the suspension at approximately 20° C. for approx. 16 h. The product is isolated by filtration, washed with cold water, dried first at approximately 20° C. in a desiccator (NaOH pellets) and finally at about 40° C. to yield colourless crystals.

Example 2.2

27.80 g of resinous 4'-[(2-fluoro-4-methoxyphenyl)methyl]-5'-methyl-1'-(1-methylethyl)-1H-pyrazol-3'-O-β-D-glucopyranoside is dissolved in THF (28 mL). TBME (190 mL) and water (1 mL) are added and the mixture is heated to reflux. The hot solution is filtered and in the filtrate crystallization is induced by scratching with a glass rod or by inoculating with seed crystals. Crystallisation is completed by stirring at approximately 20° C. for 15 h. The product is isolated by filtration, washed with TBME and dried at 40 to 50° C.

Example 2.3

16 mL THF is added to 28 g of resinous 4'-[(2-fluoro-4-methoxyphenyl)methyl]-5'-methyl-1'-(1-methylethyl)-1H-pyrazol-3'-O-β-D-glucopyranoside. TBME (100 mL) is added and the mixture is warmed to 50° C. Water (1.1 mL) and further TBME (120 mL) are added at 50° C. to the clear solution. The hot solution is then seeded and cooled to 30° C. within 1 h. Alternatively crystallization may be induced by scratching with a glass rod for example. The resulting thick suspension is further cooled to approx. 0° C. and is stirred at this temperature for 2.5 h. It is then filtered, washed with cold TBME and dried at 45° C. to yield a crystalline product.

Example 2.4

28 g resinous 4'-[(2-fluoro-4-methoxyphenyl)methyl]-5'-methyl-1'-(1-methylethyl)-1H-pyrazol-3'-O-β-D-glucopyranoside is dissolved in a mixture of THF (26 ml) and water (2.1 ml) at 60° C. TBME (150 mL) is added and the hot mixture is filtered. Insolubles are washed with TBME (50 ml). The combined turbid filtrate is again heated and the resulting solution is seeded and cooled to room temperature (approx. 20° C.) within 1.5 h. Instead of using seed crystals crystallization may be started by scratching with a glass rod for example. The resulting thick suspension is further cooled to 0° C. and stirred for 1.5 h before filtering. The product is washed with TBME (30 ml) and is finally dried at 40° C. to yield colourless crystals.

Example 2.5

33 g resinous 4'-[(2-fluoro-4-methoxyphenyl)methyl]-5'-methyl-1'-(1-methylethyl)-1H-pyrazol-3'-O-β-D-glucopyranoside is dissolved in 150 ml n-butyl acetate at approx. 80° C. The solution is filtered over charcoal which is washed with further hot 50 ml n-butyl acetate. Water (2.1 ml) is added to the combined warm filtrates at 30° C. The solution is seeded and stirred at 0° C. for 16 h. 300 ml TBME are added to the resulting suspension within 10 minutes. The mixture is cooled to −6° C. and stirred for 1 h before filtering. The solid is washed with TBME (200 ml) and is then dried at 50° C. over night to yield colourless crystals.

Example 2.6

At 60° C. 1-butanol (450 mL) and n-heptane (1.50 L) are added to crude 4'-[(2-fluoro-4-methoxyphenyl)methyl]-5'-methyl-1'-(1-methylethyl)-1H-pyrazol-3'-O-β-D-glucopyranoside (ca. 237 g), preferably as obtained by a process according to Example 1.9b. The mixture is filtered and the filter is washed with a mixture of 1-butanol (1.20 L) and n-heptane (3.75 L). Water (33.9 g) is added and the filtrate is cooled to 40° C. and seeded. Alternatively crystallization may be induced by scratching with a glass rod for example. The solution is slowly cooled to 0° C. (15 h). The product is isolated by centrifugation and washed with a cold mixture of 1-butanol and n-heptane. The product is dried in a vacuum dryer at 40 to 50° C.

The invention claimed is:
1. A pharmaceutical composition, comprising crystalline 1'-(1-methylethyl)-4'-[(2-fluoro-4-methoxyphenyl)methyl]-5'-methyl-1H-pyrazol-3'-O-β-D-glucopyranoside having an X-ray powder diffraction pattern that comprises peaks at 5.35, 9.31, 10.76, 16.20, and 19.81 degrees 2θ (±0.1 degrees 2θ), wherein said X-ray powder diffraction pattern is obtained with $CuK_{\alpha 1}$ radiation and a pharmaceutically acceptable carrier.

2. A method of treating a disease or condition which can be influenced by inhibiting the sodium-dependent glucose cotransporter, said method comprising administering to a patient in need thereof a therapeutically effective amount of a pharmaceutical composition according to claim 1.

3. A method of treating a metabolic disorder selected from the group consisting of type 1 diabetes mellitus, type 2 diabetes mellitus, impaired glucose tolerance, hyperglycemia, postprandial hyperglycemia, overweight, obesity, including class I obesity, class II obesity, class III obesity, visceral obesity and abdominal obesity, and metabolic syndrome in a patient in need thereof, said method comprising administering to a patient in need thereof a therapeutically effective amount of a pharmaceutical composition according to claim 1.

4. A method of improving glycemic control and/or reducing of fasting plasma glucose, of postprandial plasma glucose and/or of glycosylated hemoglobin HbA1c in a patient in need thereof, said method comprising administering to a patient in need thereof a therapeutically effective amount of a pharmaceutical composition according to claim 1.

5. A method of treating a complication of diabetes mellitus, selected from the group consisting of a cataract, nephropathy, retinopathy, neuropathy, tissue ischaemia, arteriosclerosis, myocardial infarction, stroke, and peripheral arterial occlusive disease, said method comprising administering to a patient in need thereof a therapeutically effective amount of a pharmaceutical composition according to claim 1.

6. A method of treating impaired glucose tolerance, insulin resistance and/or delaying the progression from metabolic syndrome to type 2 diabetes mellitus in a patient in need thereof, said method comprising administering a therapeutically effective amount of a pharmaceutical composition according to claim 1.

7. A method of reducing the weight or preventing an increase of the weight or facilitating a reduction of the weight in a patient in need thereof, said method comprising administering a therapeutically effective amount of a pharmaceutical composition according to claim 1.

8. A method of treating the degeneration of pancreatic beta cells and/or the decline of the functionality of pancreatic beta cells and/or for improving and/or restoring the functionality of pancreatic beta cells and/or restoring the functionality of pancreatic insulin secretion in a patient in need thereof, said method comprising administering a therapeutically effective amount of a pharmaceutical composition according to claim 1.

9. A method of maintaining and/or improving the insulin sensitivity and/or for treating or preventing hyperinsulinemia and/or insulin resistance in a patient in need thereof, said method comprising administering a therapeutically effective amount of a pharmaceutical composition according to claim 1.

10. A method of treating a disease or condition attributed to an abnormal accumulation of liver fat in a patient in need thereof, said method comprising administering a therapeutically effective amount of a pharmaceutical composition according to claim 1.

11. A pharmaceutical composition according to claim 1, wherein said crystalline 1'-(1-methylethyl)-4'-[(2-fluoro-4-methoxyphenyl)methyl]-5'-methyl-1H-pyrazol-3'-O-β-D-glucopyranoside comprises water in an amount of 0 to 10 weight-%.

12. A pharmaceutical composition according to claim 1, wherein said crystalline 1'-(1-methylethyl)-4'-[(2-fluoro-4-methoxyphenyl)methyl]-5'-methyl-1H-pyrazol-3'-O-β-D-glucopyranoside comprises water in an amount of about 0.5 to 4.0 weight-% at a relative humidity between 30 and 50%.

13. A pharmaceutical composition according to claim 1, wherein at least 50% by weight of all of said 1'-(1-methylethyl)-4'-[(2-fluoro-4-methoxyphenyl)methyl]-5'-methyl-1H-pyrazol-3'-O-β-D-glucopyranoside present is said crystalline 1'-(1-methylethyl)-4'-[(2-fluoro-4-methoxyphenyl)methyl]-5'-methyl-1H-pyrazol-3'-O-β-D-glucopyranoside.

14. A pharmaceutical composition according to claim 1, wherein said X-ray powder diffraction pattern of said crystalline of 1'-(1-methylethyl)-4'-[(2-fluoro-4-methoxyphenyl)methyl]-5'-methyl-1H-pyrazol-3'-O-β-D-glucopyranoside further comprises peaks at 14.27, 18.25, and 23.27 degrees 2θ (±0.1 degrees 2θ).

15. A pharmaceutical composition according to claim 14, wherein said crystalline 1'-(1-methylethyl)-4'-[(2-fluoro-4-methoxyphenyl)methyl]-5'-methyl-1H-pyrazol-3'-O-β-D-glucopyranoside comprises water in an amount of 0 to 10 weight-%.

16. A pharmaceutical composition according to claim 14, wherein said crystalline 1'-(1-methylethyl)-4'-[(2-fluoro-4-methoxyphenyl)methyl]-5'-methyl-1H-pyrazol-3'-O-β-D-glucopyranoside comprises water in an amount of about 0.5 to 4.0 weight-% at a relative humidity between 30 and 50%.

17. A pharmaceutical composition according to claim 14, wherein at least 50% by weight of all of said 1'-(1-methylethyl)-4'-[(2-fluoro-4-methoxyphenyl)methyl]-5'-methyl-1H-pyrazol-3'-O-β-D-glucopyranoside present is said crystalline 1'-(1-methylethyl)-4'-[(2-fluoro-4-methoxyphenyl)methyl]-5'-methyl-1H-pyrazol-3'-O-β-D-glucopyranoside.

18. A method of treating a disease or condition which can be influenced by inhibiting the sodium-dependent glucose cotransporter, said method comprising administering to a patient in need thereof a therapeutically effective amount of a pharmaceutical composition according to claim 14.

19. A method of treating a metabolic disorder selected from the group consisting of type 1 diabetes mellitus, type 2 diabetes mellitus, impaired glucose tolerance, hyperglycemia, postprandial hyperglycemia, overweight, obesity, including class I obesity, class II obesity, class III obesity, visceral obesity and abdominal obesity, and metabolic syndrome in a patient in need thereof, said method comprising administering to a patient in need thereof a therapeutically effective amount of a pharmaceutical composition according to claim 14.

20. A method of improving glycemic control and/or reducing of fasting plasma glucose, of postprandial plasma glucose and/or of glycosylated hemoglobin HbA1c in a patient in need thereof, said method comprising administering to a patient in need thereof a therapeutically effective amount of a pharmaceutical composition according to claim 14.

21. A method of treating a complication of diabetes mellitus, selected from the group consisting of a cataract, nephropathy, retinopathy, neuropathy, tissue ischaemia, arteriosclerosis, myocardial infarction, stroke, and peripheral arterial occlusive disease, said method comprising administering to a patient in need thereof a therapeutically effective amount of a pharmaceutical composition according to claim 14.

22. A method of treating impaired glucose tolerance, insulin resistance and/or delaying the progression from metabolic syndrome to type 2 diabetes mellitus in a patient in need thereof, said method comprising administering a therapeutically effective amount of a pharmaceutical composition according to claim 14.

23. A method of reducing the weight or preventing an increase of the weight or facilitating a reduction of the weight in a patient in need thereof, said method comprising administering a therapeutically effective amount of a pharmaceutical composition according to claim 14.

24. A method of treating the degeneration of pancreatic beta cells and/or the decline of the functionality of pancreatic beta cells and/or for improving and/or restoring the functionality of pancreatic beta cells and/or restoring the functionality of pancreatic insulin secretion in a patient in need thereof, said method comprising administering a therapeutically effective amount of a pharmaceutical composition according to claim 14.

25. A method of maintaining and/or improving the insulin sensitivity and/or for treating or preventing hyperinsulinemia and/or insulin resistance in a patient in need thereof, said method comprising administering a therapeutically effective amount of a pharmaceutical composition according to claim 14.

26. A method of treating a disease or condition attributed to an abnormal accumulation of liver fat in a patient in need thereof, said method comprising administering a therapeutically effective amount of a pharmaceutical composition according to claim 14.

* * * * *